(12) United States Patent
De Groot et al.

(10) Patent No.: US 9,233,189 B2
(45) Date of Patent: Jan. 12, 2016

(54) HYDROXYAPATITE TISSUE FILLER AND ITS PREPARATION AND USE

(71) Applicant: CAM BIOCERAMICS B.V., CL Leiden (NL)

(72) Inventors: Klaas De Groot, Heemstede (NL); Nienke de Roode-Beuling, Delft (NL); Nol Van De Mortel, Wassenaar (NL); Mariska Bezemer, Oegstgeest (NL)

(73) Assignee: Cam Bioceramics B.V., CL Leiden (NL)

( * ) Notice: Subject to any disclaimer, the term of this patent is extended or adjusted under 35 U.S.C. 154(b) by 0 days.

(21) Appl. No.: 13/684,912

(22) Filed: Nov. 26, 2012

(65) Prior Publication Data

US 2013/0149348 A1    Jun. 13, 2013

Related U.S. Application Data

(63) Continuation of application No. 12/444,514, filed as application No. PCT/NL2007/050479 on Oct. 4, 2007, now abandoned.

(60) Provisional application No. 60/849,485, filed on Oct. 5, 2006.

(30) Foreign Application Priority Data

Oct. 5, 2006  (EP) .................................. 06121834

(51) Int. Cl.
*A61L 27/12*  (2006.01)
*A61K 33/42*  (2006.01)
*A61L 27/42*  (2006.01)

(52) U.S. Cl.
CPC .................. *A61L 27/12* (2013.01); *A61K 33/42* (2013.01); *A61L 27/425* (2013.01)

(58) Field of Classification Search
None
See application file for complete search history.

(56) References Cited

U.S. PATENT DOCUMENTS

| 4,803,075 | A | 2/1989 | Wallace et al. |
| 5,352,715 | A | 10/1994 | Wallace et al. |
| 6,425,949 | B1 | 7/2002 | Lemaitre et al. |
| 6,537,574 | B1 | 3/2003 | Hubbard |
| 7,754,246 | B2 | 7/2010 | Moseley et al. |
| 2004/0024081 | A1* | 2/2004 | Trieu et al. ................... 523/113 |
| 2005/0241535 | A1* | 11/2005 | Bohner ........................ 106/690 |
| 2009/0220475 | A1 | 9/2009 | Bohner et al. |

FOREIGN PATENT DOCUMENTS

| WO | WO-93/15721 | 8/1993 |
| WO | WO-93/16657 | 9/1993 |
| WO | WO2007/056872 | * 5/2007 |

OTHER PUBLICATIONS

Temenoff et al. "Injectable biodegradable materials for orthopedic issue engineering", Biomaterials, 21, 2000, pp. 2405-2412.*
Zhu et al "Hydroxyapatite nanoparticles as novel gene carrier", Journal of Nanoparticle Research, 6, 2004, pp. 307-311.*
Temenoff et al. "Injectable biodeqradeable materials for orthopedic issue engineering", Biomaterials, 21,2000, 2405-2412.*
Bohner, et al. "Injectability of calcium phosphate pastes", Biomaterials, 2005, vol. 26, pp. 1553-1563.
De Boulle, "Management of complications after implantation of fillers", J. Cosmetic Dermatology, 2004, vol. 3, pp. 2-15.
Haneke, "Skin rejuvenation without a scalpel. I. Fillers", J. Cosmetic Dermatology, 2005, vol. 5, pp. 157-167.
International Search Report in PCT/NL2007/050479 dated Feb. 19, 2009.

* cited by examiner

*Primary Examiner* — Bethany Barham
*Assistant Examiner* — Melissa Javier
(74) *Attorney, Agent, or Firm* — Foley & Lardner LLP; Sunit Talapatra

(57) ABSTRACT

The invention pertains to a biocompatible composition, suitable for use in soft or hard tissue augmentation, wherein the composition is an aqueous suspension containing a carrier fraction of ceramic particles of less than 15 μm and an augmentation fraction of ceramic particles of at least 20 μm. The ceramics typically include calcium phosphate. The composition is a may be used in soft tissue repair as well as hard bone replacement. It advantageously avoids the need for foreign body materials which are conventionally applied to stabilize augmentation suspensions.

13 Claims, No Drawings

HYDROXYAPATITE TISSUE FILLER AND ITS PREPARATION AND USE

FIELD OF THE INVENTION

The invention pertains to biocompatible compositions containing ceramic particles, in particular hydroxyapatite, for soft and hard tissue augmentation, especially for bone regeneration and treatment of skin contour deficiencies, and for cosmetic use in plastic surgery, in particular for filling soli tissue voids or creating soft tissue augmentation.

BACKGROUND OF THE INVENTION

Since long biocompatible materials have beers applied in augmenting soft tissue in the practice of plastic and reconstructive surgery. These biomaterials are commonly delivered to the tissue site where augmentation is desired by means of an injectable composition that comprises biomaterial and a biocompatible fluid, wherein the fluid acts as a lubricant to improve the delivery of the biomaterial suspension.

Since the mid-eighties polymethylmethacrylate (PMMA) has been studied as a soft tissue augmentation device, replacing then popular collagen. The permanent character of PMMA and many other fillers such as silicones would make repetitious corrections unnecessary. However, it is discovered recently that the injection of PMMA microspheres causes all kinds of complications in time, to a large extent related to the non-biodegradable properties. Moreover, it is now believed that the permanent impact of filler materials in tissue is undesired, since the tissue itself is subject to ageing (see e.g. E. Haneke, "*Skin rejuvenation without a scalpel I. Fillers*", J Cosmetic Dermatology; 5; 15-167 (2005): K. De Boulle, "*Management of complications after impantation of fillers*", J Cosmetic Dermatology; 3:2-15 (2004).

WO-A-93/16657 teaches the use of injectable ceramic compositions comprising biocompatible ceramic materials such as calcium hydroxyapatite in a fluid carrier. These ceramics show excellent performance in repair and augmentation of soft and hard tissues. Further, hydroxyapatite has very low immunogenicity. The 50-250 μm sized ceramic particles are stabilized in a viscous or even gel-like organic polymer, such as polyethylene glycol, hyaluronic acid, poly (hydroxyethyl methacrylate), or in a collagen hydrogel.

Of about the same time, WO-A-93/15721 discloses a matrix of smooth, rounded, substantially spherical, finely divided particles of calcium hydroxyapatite in a biocompatible, resorbable lubricious gel carrier comprising a polysaccharide. The particles are typically in the range of 35-150 μm to minimize the possibility of particle migration by phagocytosis and to facilitate injectability. The carrier serves to further improve the delivery of the augmentation material by injection to the tissue site where augmentation is desired, and is typically formed from water, about 25 wt % glycerin and sodium carboxymethyl cellulose. It enables the ceramic particles to remain in suspension without settling for an indefinite period of time until used, more specifically at least about 6 months. U.S. Pat. No. 4,803,075 suggests the use of further biocompatible fluid lubricants and/or viscosity modifiers, such as glycogen, maltose and the like.

However, the use of foreign body carrier materials renders these injectable hydroxyapatite compositions unattractive. In the art there is a continuous need to improve biocompatible implant materials tor soil and hard tissue repair and augmentation, wherein the use of foreign body materials is minimised or even avoided. The ideal soft tissue filler would be non-permanent biocompatible, have minimal side effects, not require allergy testing, be easy to use/inject, be painless to inject, and be cost-effective for both the physician and the patient.

SUMMARY OF THE INVENTION

It is an object of the invention to provide a biocompatible composition for use in soft and hard tissue repair and augmentation comprising a minimal amount of foreign matters, and which composition has a low immunogenicity.

It is a further object of the invention to provide: such a biocompatible composition that, if applied in soft tissue augmentation, is resorbable over time periods of 1-2 years in a human being of about 40 years of age. If applied in hard tissue augmentation material, it should dissolve in the human body overtime, but slow enough so as to allow for replacement with growing tissue cells.

The invention thus pertains to a biocompatible composition, suitable for use in soft or hard tissue augmentation, wherein, the composition is an aqueous suspension containing a carrier fraction of ceramic particles of less than 15 μm and an augmentation fraction of ceramic particles of at least 20 μm. The ceramic particles of the two fractions together preferably make up for more than 95 wt %, more preferably more than 98 wt % of the total solids of the composition. The invention especially pertains to such a composition tor medical use as a therapeutic agent.

Throughout the text, particle sizes apply to the largest dimension of the particle, unless stated otherwise.

It is now found that it is possible to stabilize augmentation particles, independent of their size and porosity, by adding then to an aqueous gel or suspension of small, unagglomerated ceramic particles. Undesired conventional stabilizing agents can be dispensed with.

DETAILED DESCRIPTION OF THE INVENTION

Throughout the description and claims, the term "gel" or "suspension" is used to refer to the mix of carrier particles in water, while the terms "composition" refers to the mixture of augmentation particles and the aforementioned gel or suspension. It is noted that the biocompatible composition in itself may also be characterized as a suspension. In the context of the invention, the different wording is merely intended to distinguish between the ready-to-use composition and its precursor.

The ceramic particles preferably comprise calcium phosphate, calcium silicate, calcium carbonate or fluorides. The ceramic material is preferably a calcium phosphate, particularly comprising hydroxyapatite, also known as basic calcium phosphate, which is the natural mineral phase of teeth and bones. As an implant material, granular hydroxyapatite, has proven to be highly compatible in tissue. Known hydroxyapatite derivatives are included. Examples include, but are not limited to, tetracalcium phosphate, calcium pyrophosphate, tricalcium phosphate, octacalcium phosphate, calcium fluorapatite, calcium carbonate apatite, and combinations thereof. Other equivalent calcium-based compositions can also be used, such as calcium carbonate, and the like. These materials are commercially available, and a selection can be made from a number of mesh sizes and porosities. The choice of material is regardless of the microstructure, protionation status of the phosphate, or extent of hydration.

While the mineral content of bone could be harvested and purified for this purpose, the use of industrially produced calcium phosphate mineral particles is preferable, because of its more predictable quality.

In the context of the invention, the larger particles are considered as the "augmentation particles", and will addressed as such from now on. These augmentation particles are suspended under aqueous conditions. It is found that such aqueous matrix comprising augmentation particles may be stabilized by a fraction of smaller particles of the same or another biocompatible ceramic material. Stabilisation is required to homogenize the ceramic augmentation particles for an indefinite amount of time, at least sufficiently long to allow further processing and to inject the composition.

Hence, the smaller ceramic particles take over the role of the lubricous gel carrier of non-ceramic materials presently applied in the art for stabilization, homogenization and lubrication purposes, and may thus beneficially replace the conventional foreign body carrier materials or lubricants. For sake of simplicity, these smaller particles of biocompatible ceramic material are referred to as "carrier particles" in the context of the invention. These may be applied in compositions for either soft or hard tissue augmentation, which compositions mainly vary in the type, size and amount of augmentation particles present therein. The invention rests in the combination of these conventional augmentation materials with the carrier particles as characterized here below.

The use of these carrier particles as stabilizing material in a biocompatible composition in tissue augmentation is unobvious, especially since it is taught in the art that small-sized augmentation materials would, upon injection, induce phagocytosis in the organism body and should thus be avoided. The potential of these small particles to homogenize and stabilize augmentation materials is nowhere mentioned.

In one embodiment, the carrier particles are preferably larger than 100 nm. More preferably, these carrier particles have an average size larger than 1 µm. Preferably, the carrier particles have a size of less than 10 µm. Best results are obtained with carrier particles smaller than 5 µm.

In another embodiment, the carrier particles are preferably smaller than 1000 nm, more preferably 20-500 nm, in particular 25-300 nm.

The carrier fraction preferably comprises hydroxyapatite (HA) and/or TCP. These carrier particulars may be obtained from commercially available grades of ceramics, by conventional sieving, micromotion or precipitation from calcium nitrate and ammonium phosphate. The precipitate may be spray dried and/or sintered (i.e. calcinated). Alternatively, the precipitate may be processed by centrifugation and optional sifting. Where the desired particles are obtained by sieving, this may be performed by "wet" or "dry" sieving. The particle size is predominantly determined by the selection of the starting material. Sieving and precipitation techniques are equally well applicable. Where a softer gel of augmentation particles is desired, it is preferred to use carrier particles as obtained by precipitation.

Since the carrier particles contribute to the stability of the composition through their surface properties, it is preferred that more than 50%, preferably more than 75%, most preferably more than 90% of the total volume of particles in the carrier fraction is in singular or unagglomerated form. Agglomeration would only hamper the particles in achieving stability in the composition. It is thus preferred to subject suitable source of carrier particles to a kind of "unagglomeration" treatment, for instance by subjecting the particles to a ball milling. This is in contrast to the augmentation particles, which could be formed by an agglomeration process.

The stability of the suspension may be further improved selecting the material for the smaller particles on the basis of its interfacial properties, which may be fine-tuned by the preparation route. Since augmentation and carrier particles are present for different reasons, these materials do not necessarily have to be of the same origin. In fact, a selection of different materials may lead to better results, provided that the augmentation and carrier particles are chosen from the above-listed biocompatible materials.

As aforementioned, the augmentation particles are in essence indifferent from those traditionally applied in bone repair and in soft tissue augmentation. The preferred ceramics for use as augmentation particles comprises HA, fluorapatite, octacalcium phosphate and TCP.

Especially when used in soft tissue augmentation, the augmentation particles comprise smooth and substantially rounded particles. These particles are preferably substantially spherical "Substantially spherical" generally means a shape that is spheroidal. When viewing any cross-section of the particle, the difference between the average major diameter and the average minor diameter is less than 20%.

Where lower resorbability rates are desired, it is preferred that the augmentation materials resemble perfect spheres, because of the optimum area-to-volume ratio and the positive effect on prevention of inflammations related therewith. The terms "rounded" or "smooth" as used herein refers to the fact even though the present particles are not perfect spheres, they do not have any sharp or angular edges, in order to improve injectability if so required. Surface milling and the like can improve surface smoothness.

The augmentation particles must be sufficiently large so as to avoid rapid degradation. Resorbtion occurs where smaller particles on the order of 15 µm or less become engulfed by the cells and removed by the lymphatic system from the site where the augmentation material has been introduced into the tissues. The augmentation particles will dissolve over time, for HA typically at a rate of 15 µm/year. The resorbtion time of the injected mass depends on the actual particle size. The upper limit of the augmentation particles is determined by its use, being in soft or hard tissue augmentation. For soft tissue augmentation purposes it is desired that the composition is injectable, meaning that the composition can easily be injected through a syringe intradermally or subcutaneously. If introduced into soli tissue by injection the upper limit of the particle see will be dictated by the particular injection equipment employed. That is, the particles must be sufficiently small so as to avoid aggregation and clogging of the syringe when being injected. A typical range for injection is from about 20 to 100 µm, mom preferably from 25-50 µm.

Where injectability is an issue, it is preferred to use a narrow or even equivalent particle size range of augmentation particles due to the fact that a distribution of such smooth and round particles reduces friction, and facilitates the ease of injecting the particles by needle from a syringe into the skin tissue at the desired augmentation site. This is in contrast to the use of the more porous, textured, irregularly shaped particles which tend to increase the frictional forces, and am much more difficult to deliver by injection. Hence, it is preferred that the size difference between the largest and the smallest (soft tissue) augmentation particle does not exceed about 35 µm. Further, it may be desirable to minimize surface porosity to below 30%; with elimination of jagged irregular surfaces, the ability of the smooth round particles to flow easily in contact with each other is maximized.

If the composition is to applied in bone repair, injectability is not an issue per se, since it may be applied there in other forms. Then, the augmentation particles are preferably much larger, typically between 100 µm and 4 mm, preferably between 1-1.5 mm. In hard tissue augmentation the surface porosity plays a more critical role. It is typically more than 30%, more preferably at least 50%, in order for the composition to provide a matrix for the ingrowth of new cartilage and bone.

The augmentation particles and carrier particles are preferably present in the composition in a weight ratio of 0.5:1 to 15:1, more preferably up to 10:1. In case of soft tissue augmentation material, the weight ratio is even more preferably higher than 2:1, most preferably 4:1 to 9:1. These ceramic particles preferably form the only source of augmentation materials present in the competition. The composition should contain a sufficient volume of the larger ceramic particles (i.e. the augmentation particles) to provide an effective base for autogeneous tissue growth. In case of a composition for use in soft tissue repair, preferably 20-40 vol % of the total composition is formed from augmentation particles. In hard tissue repair, these numbers may be higher, since fix augmentation particles are much larger, and may still be stabilized using corresponding amounts of water and carrier particles. There, it is preferred that the amount of augmentation particles is 10-60 vol % of the composition.

Since stabilization of the suspension is only achieved for distinct size distributions of small and large ceramic particles, it is essential that the biocompatible composition contains little amount of ceramic particles having a size in between that of the augmentation particles and carrier particles. It is preferred that the composition is essentially free from biocompatible ceramic particles having a size outside the aforementioned ranges. However, from a practical perspective it should be understood that "essentially free from other biocompatible ceramic particles" means that small amounts of particles outside the desired ranges is allowed for in the composition, preferably less than 10 wt %, more preferably less than 5 wt % of the total amount of ceramic particles.

Additionally or alternatively, it is preferred that the suspension is a multimodal distribution, preferably a bimodal distribution of ceramic particles, containing at least a mode of augmentation particles and a mode of carrier particles with one or more of the foregoing characteristics.

The composition is free from any resorbable lubricants as described in the art, especially from polysaccharides such as carboxylmethylcellulose equivalents thereof, and glycerin. Advantageously, the composition is free front any foreign body material conventionally applied as augmentation material or lubricant or carrier thereof. In the most preferred embodiment, all augmentation material present in the injectable biocompatible composition is a form of calcium phosphate.

In addition to the augmentation material, the composition may optionally comprise an amount of active ingredients. These active ingredients can include substances that may provide therapeutic effects to the process of augmentation or biological or physiological responses to the dermal augmentation. An example of such therapeutic agent is an anti-inflammation agent that prevents or reduces the effect of inflammations associated with dermal augmentation, an anti-bacterial, anti-fungal or anti-histamine agent. It may also involve cell adhesion promoters, which enhance the adhesiveness of cells to the surface of the particles. Another suitable active ingredient is a local anaesthetic agent. For the purpose of osteogenesis, the ceramic filler of the invention may be admixed with an osteoinductive factor (OPE), considered as one of the active ingredients optionally included in the composition. OFE useful in the composition of the invention is known to the person skilled in the art. The skilled person can easily recognize whether ingredients of the composition are included for augmentation or other purposes.

In a preferred embodiment, the biocompatible composition of the invention contains 25-70 wt % water, 75-30 wt % of the biocompatible ceramic materials, and optionally up to 5 wt % of active ingredients. If active ingredients are present, the sum of water, carrier particles, augmentation particles and active ingredients is 100 wt %.

The invention also pertains to the method of manufacturing the biocompatible composition of the invention. The composition is preferably prepared by mixing the augmentation particles and carrier particles and water at ambient conditions until all components are suspended. Therein, it is preferred that the carrier particles are suspended prior to or simultaneously with the augmentation particles.

Thereto, an aqueous suspension or gel of carrier particles is first prepared, containing 10-55 wt %, preferably 15-45 wt %, more preferably 20-35 wt % of carrier particles. Hence, the invention also pertains to an aqueous suspension or gel of carrier particles with the aforementioned characteristics, and the use thereof for stabilization of augmentation materials.

From a rheological point of view, the suspension may be characterized as being a thixotropic non-Newtonian liquid. In the literature, where for instance in U.S. Pat. No. 5,922,025 in relation to conventional glycerin-containing cellulose-polysaccharide gels containing augmentation material mention is made of a minimum gel viscosity of about 20,000 mPa·s. According to U.S. Pat. No. 5,922,025, at lower values the particles do not remain in suspension. However, with the carrier particles of the invention, it is possible to prepare a suspension having a viscosity as low as 5,000 mPa·s, and which is capable of stabilizing the biocompatible composition. Obviously, the upper limit is not particularly limited, but may be adapted to the intended use. If the composition is to be injected for soft tissue repair, it is preferred that the gel viscosity is smaller than 30,000 mPa·s. For hard tissue repair them does not appear to be such restriction.

The aqueous composition thus obtained may be sterilized by means known in the art, among which, favorably, gamma radiation. This adds an additional advantage to the composition of the invention over the aqueous gels of corresponding augmentation ceramic materials in a matrix containing polysaccharides and/or glycerine known in the art, which are said to be destroyed upon gamma sterilization. Hence, with the present composition sterilization is no longer limited to autoclaving.

The biocompatible composition may be used for regeneration of hard tissues, such as bone, cartilage, connective tissues and the like. The materials may even be formed into implants. The methods tor utilizing the composition of the invention in the repair of bones, including surgical methods of implanting, are well understood in the art, and the compositions of the invention are useful in employing these standard means.

However, in the preferred embodiment the composition of the invention is applied in soft tissue augmentation. Hence, the present invention encompasses the use of the biocompatible compositions to treat skin deficiencies caused by diseases such as acne, cancer and lipodystrophy syndrome. Further, the invention encompasses the treatment of scars on or within the skin caused by accidents, wounds and injuries. The skin deficiencies may also be the result of the treatment of a disease. The dermal augmentation method of the invention is also suitable for the treatment of skin contour deficiencies, which are often caused by aging, environmental exposure, weight loss, child bearing, injury and surgery.

Suitable for the treatment by the method of the present invention are contour deficiencies such as frown lines, worry lines, wrinkles, crow's feet, marionette lines, stretch marks, and internal and external scars resulted from injury, wound, bite, surgery, or accident. The invention works particularly well with contour deficiencies of such areas as cheeks, nose, forehead and neck.

The biocompatible compositions may also be applied to augment internal tissues such as tissue defining sphincters in the treatment of incontinence, and for the treatment of unilateral vocal cord paralysis.

The invention further pertains to a process of cosmetically improving the bodily appearance of a mammal, comprising introducing to the mammal's body subcutaneously or intradermally the composition of the invention in injectable form. The composition is preferably injected at one of the aforementioned places into the mammal's body. The mammal is preferably a human being.

The invention also pertains to a kit for one of the aforementioned applications, where the augmentation particles, the carrier particles and other optional components are packaged in ready-to-use syringes, for instance those as described above.

EXAMPLES

Example 1

Gel of Precipitated Amorphous Hydroxypatite Carrier Particles

Calcium phosphate (amorphous hydroxypatite) particles are obtained by precipitation from calcium nitrate and ammonium phosphate. The resulting particles were less than 1 μm in size. After cleaning, a gel-like suspension was obtained.

In this case, the gel contained, prior to mixing with the augmentation material, 35 wt % carrier particles and 65 wt % water.

The augmentation particles were produced by spray-drying a slurry of precipitated calcium phosphate, as described above, and then sintered and sieved to obtain particles of 25-45 μm.

Upon mixing of 14 ml of the gel with 18.84 g augmentation particles a mix of 17.2 wt % carrier particles, 31.9 wt % water and 50.9 wt % augmentation particles was obtained. The weight ratio of augmentation particles to carrier particles was 3:1. Carrier particles and water together formed 70 vol % of the stable suspension.

Example 2

Porous Augmentation Particles for Hard Tissue Augmentation

The gel obtained as described in example 1 was used.

6.25 g of the gel thus obtained was mixed with 1.20 g augmentation particles (80% porous, 1-4 mm hydroxypatite granulate material (CAM Implants, Leiden, the Netherlands).

The gel contained 35 wt % carrier particles and 65 wt % water, the mix contained 29.4 wt % carrier particles and 54.5 wt % water and 16.1 wt % augmentation particles. The weight ratio of augmentation particles to carrier panicles was 0.5:1.

Example 3

Dense Augmentation Particles with a Gel of Calcinated Calcium Phosphate in Water Calcium phosphate in spray-dried form was calcinated at about 400° C. and then an average particle size of about 2-3 μm was obtained. After washing, 20 g of these particles were suspended in 100 g water, yielding a gel of 17 wt % carrier particles in 83 wt % water, 3.42 g of the gel was mixed with 4.89 g augmentation particles (dense, 0.5-2 mm HA granulate (CAM Implants). The biocompatible composition thus obtained contained 7.0 wt % carrier particles, 34.2 wt % water and 58.8 wt % hard tissue augmentation particles. The weight ratio of augmentation particles:carrier particles=8:1. The mixture contained 34 vol % of augmentation particles, in terms of the total volume of the composition.

The invention claimed is:

1. An injectable biocompatible aqueous suspension or gel consisting of 15-45 wt % ceramic hydroxyapatite particles with a size between 20 and 500 nm, water, and optionally, at least one therapeutic substance selected from the group consisting of an anti-inflammation agent, an antibacterial agent, an antifungal agent, an anti-histamine agent, a cell adhesion promoter, a local anesthetic agent and an osteoinductive factor.

2. The suspension or gel according to claim 1, containing 20-35 wt % of said ceramic particles.

3. The suspension or gel according to claim 1, wherein said ceramic particles are between 100 nm and 500 nm.

4. The suspension or gel according claim 1, wherein more than 50% of the total volume of said ceramic particles is in singular form.

5. The suspension or gel according to claim 1, wherein the suspension or gel is sterile.

6. The suspension or gel according to claim 1, wherein the ceramic particles have a size of 25-300 nm.

7. The suspension or gel according to claim 1, containing 15-35 wt % of said ceramic particles.

8. The suspension or gel according to claim 6, containing 15-35 wt % of said ceramic particles.

9. A method of treatment comprising introducing to a mammalian subject the composition according to claim 1.

10. The method according to claim 9, wherein the treatment is for bone regeneration and/or of skin contour deficiencies.

11. The method according to claim 10, wherein said skin contour deficiencies are at least one of frown lines, worry lines, wrinkles, crow's feet, marionette liens, stretch marks, or the result of ageing, environmental exposure, weight loss, child bearing, injury, surgery, acne, cancer, lipodystrophy, syndrome, or scars on or within the skin caused by accidents, wounds or injuries.

12. The method according to claim 9, wherein the treatment is plastic and reconstructive surgery.

13. A method for hard tissue augmentation and regeneration and hard tissue repair, surgical methods and implanting, comprising introducing to a mammal's body the composition according to claim 1.

* * * * *